United States Patent
Eo et al.

(10) Patent No.: US 11,229,586 B2
(45) Date of Patent: Jan. 25, 2022

(54) SURFACTANT-FREE COSMETIC COMPOSITION

(71) Applicant: AMOREPACIFIC CORPORATION, Seoul (KR)

(72) Inventors: Seong Chan Eo, Yongin-si (KR); Seung Han Park, Yongin-si (KR); Byung Fhy Suh, Yongin-si (KR); Ji Sik Shin, Yongin-si (KR); Dong Won Choi, Yongin-si (KR); Byung Guen Chae, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 16/901,233

(22) Filed: Jun. 15, 2020

(65) Prior Publication Data

US 2020/0405592 A1 Dec. 31, 2020

(30) Foreign Application Priority Data

Jun. 25, 2019 (KR) .......................... 10-2019-0075350

(51) Int. Cl.
| | |
|---|---|
| *A61K 8/06* | (2006.01) |
| *A61K 8/895* | (2006.01) |
| *A61K 8/891* | (2006.01) |
| *A61K 8/67* | (2006.01) |
| *A61K 8/37* | (2006.01) |
| *A61K 8/362* | (2006.01) |
| *A61K 8/365* | (2006.01) |
| *A61K 8/368* | (2006.01) |
| *A61K 8/42* | (2006.01) |
| *A61Q 19/02* | (2006.01) |
| *A61Q 17/04* | (2006.01) |
| *A61K 8/898* | (2006.01) |

(52) U.S. Cl.
CPC .............. *A61K 8/064* (2013.01); *A61K 8/362* (2013.01); *A61K 8/365* (2013.01); *A61K 8/368* (2013.01); *A61K 8/37* (2013.01); *A61K 8/42* (2013.01); *A61K 8/675* (2013.01); *A61K 8/676* (2013.01); *A61K 8/891* (2013.01); *A61K 8/895* (2013.01); *A61K 8/898* (2013.01); *A61Q 17/04* (2013.01); *A61Q 19/02* (2013.01); *A61K 2800/33* (2013.01); *A61K 2800/41* (2013.01)

(58) Field of Classification Search
CPC ...................................................... A61K 8/064
See application file for complete search history.

(56) References Cited

U.S. PATENT DOCUMENTS

| | | | | |
|---|---|---|---|---|
| 2002/0136771 A1* | 9/2002 | Parr | ...................... | A61K 31/375 424/488 |
| 2004/0258721 A1* | 12/2004 | Bauer | ...................... | A61K 7/00 424/401 |
| 2006/0269499 A1 | 11/2006 | Gormley et al. | | |
| 2010/0203097 A1 | 8/2010 | Tanaka | | |
| 2012/0237583 A1 | 9/2012 | Hayashi et al. | | |
| 2013/0345316 A1* | 12/2013 | Chiou | .................... | A61K 8/891 8/891 |
| 2014/0315995 A1* | 10/2014 | Dreher | ................. | A61K 31/375 31/375 |
| 2017/0349712 A1* | 12/2017 | Shin | .......................... | C08J 3/12 3/126 |
| 2019/0388306 A1* | 12/2019 | Ravni | ..................... | A61K 8/02 8/229 |

FOREIGN PATENT DOCUMENTS

| | | | | |
|---|---|---|---|---|
| JP | 2008-297239 A | 12/2008 | | |
| JP | 2008297239 A | * 12/2008 | ............... | A61K 8/24 |
| JP | 2009-149555 A | 7/2009 | | |
| JP | 2009-149556 A | 7/2009 | | |
| JP | 2016-056150 A | 4/2016 | | |
| KR | 10-2007-0079166 A | 8/2007 | | |
| KR | 10-2012-0096543 A | 8/2012 | | |
| KR | 10-1291839 B1 | 7/2013 | | |
| KR | 10-1483974 B1 | 1/2015 | | |
| KR | 10-2016-0070048 A | 6/2016 | | |
| KR | 10-2016-0081824 A | 7/2016 | | |
| KR | 10-2017-0087808 A | 7/2017 | | |
| KR | 10-2018-0076180 A | 7/2018 | | |
| KR | 10-1908347 B1 | 10/2018 | | |
| KR | 10-2019-0013007 A | 2/2019 | | |

(Continued)

OTHER PUBLICATIONS

Eo, Seong Chan, Stabilization of W/S (O) emulsion using PCA Dimethicone and silicone powder, The Polymer Society of Korea. (Year: 2019).*

(Continued)

*Primary Examiner* — Mark V Stevens
*Assistant Examiner* — Alparslan Asan
(74) *Attorney, Agent, or Firm* — Sughrue Mion, PLLC

(57) ABSTRACT

A surfactant-free cosmetic composition is disclosed. The composition is a stable water in silicone oil (W/S) formulation containing a silicone oil phase portion and an aqueous phase portion, wherein the silicone oil phase portion contains an emollient having a pyrrolidone carboxylic acid group, oil-absorbing powder and silicone oil, and the aqueous phase portion contains 50 wt.% or more of water based on the total weight of the surfactant-free cosmetic composition. The composition may further contain a high content of vitamin C or a vitamin C derivative and has improved long term storage stability.

17 Claims, 7 Drawing Sheets

(56) References Cited

FOREIGN PATENT DOCUMENTS

| KR | 10-2019-0046740 A | 5/2019 | | |
|---|---|---|---|---|
| WO | WO0103664 A1 * | 1/2001 | ............... | A61K 7/48 |
| WO | WO2018142076 A1 * | 8/2018 | ............... | A61K 8/37 |

OTHER PUBLICATIONS

SAAPedia, PCA Dimethicone—Surfactant—SAAPedia. (Year: 2014).*
JP2008297239A, Google English translation, downloaded Nov. 2020 (Year: 2020).*
Eo, Seong Chan, "Stabilization of W / S (O) emulsion using PCA Dimethicone and silicon powder", The Polymer Society Of Korea, Oct. 2019, p. 77-77, vol. 44, No. 2.

* cited by examiner

[FIG. 1]
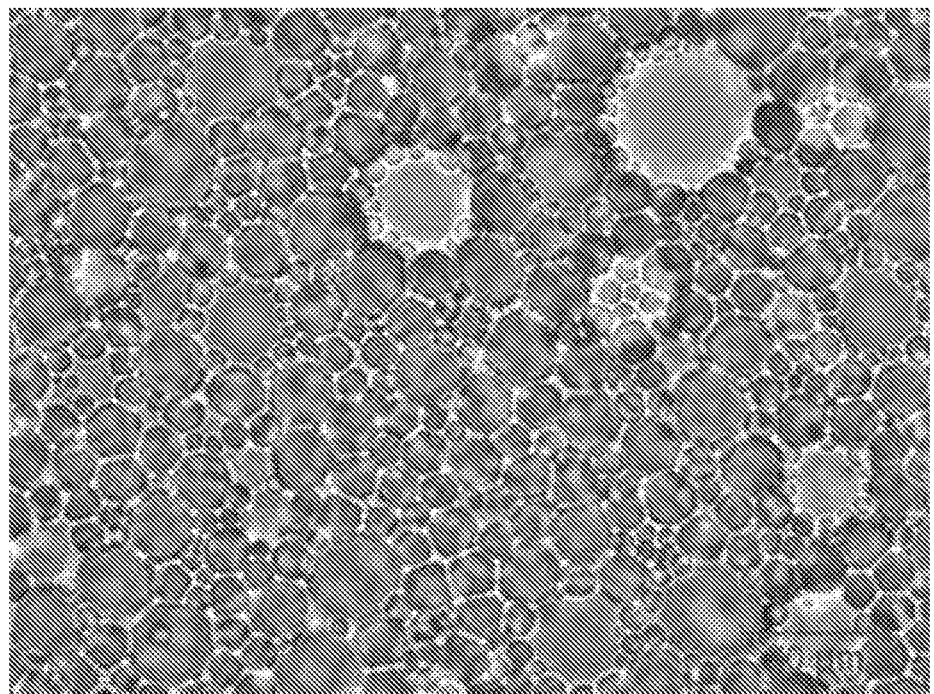
[FIG. 2]
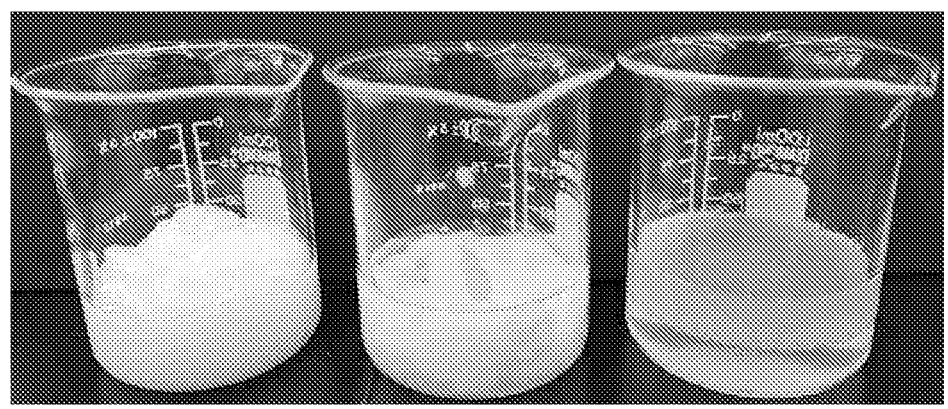

[FIG. 3]

[FIG. 4]
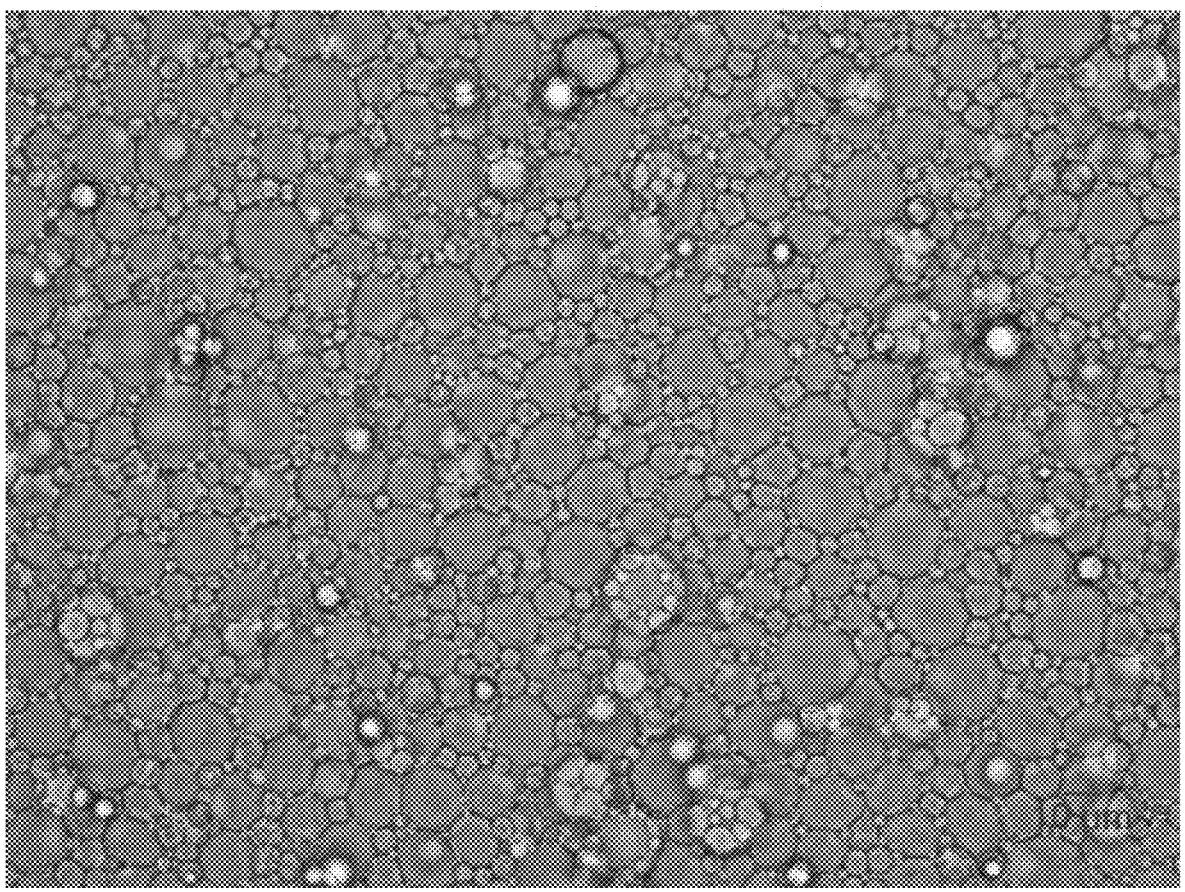

[FIG. 5]
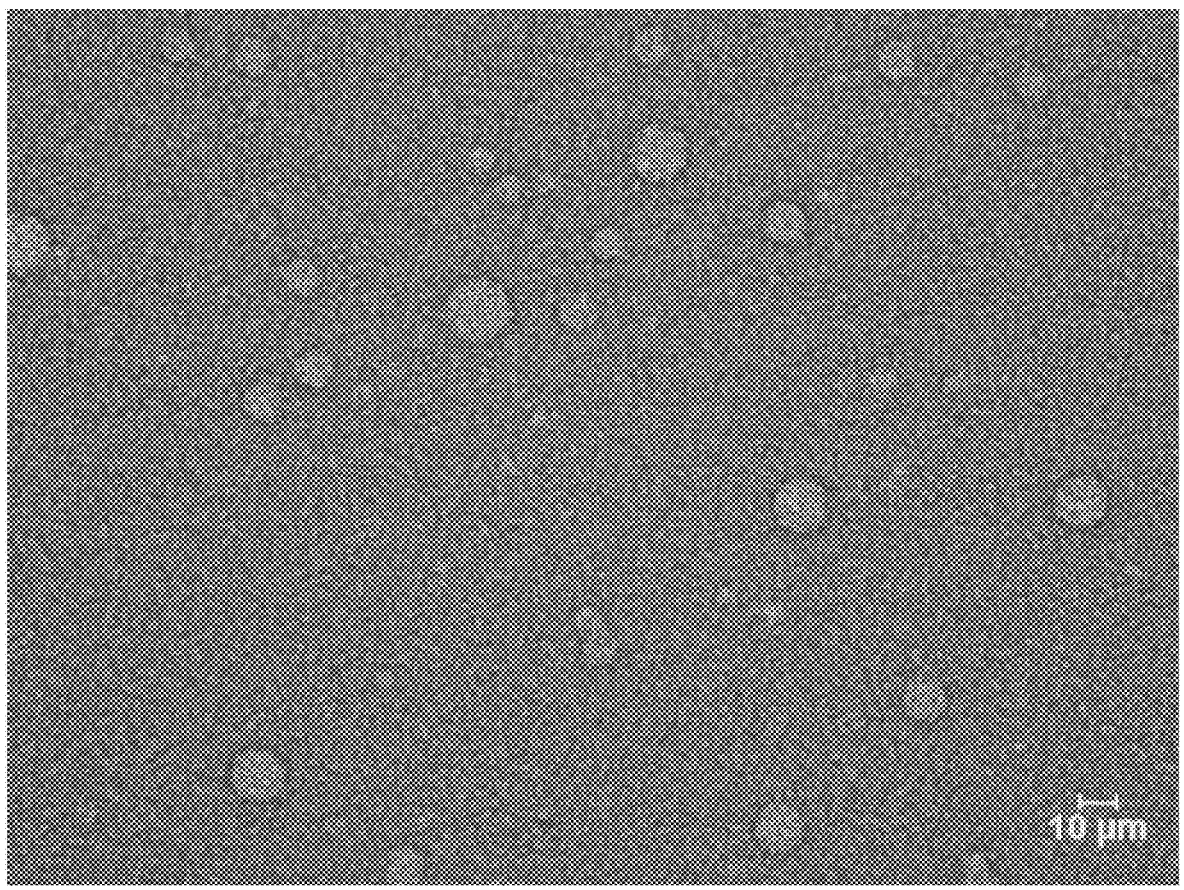

[FIG. 6]
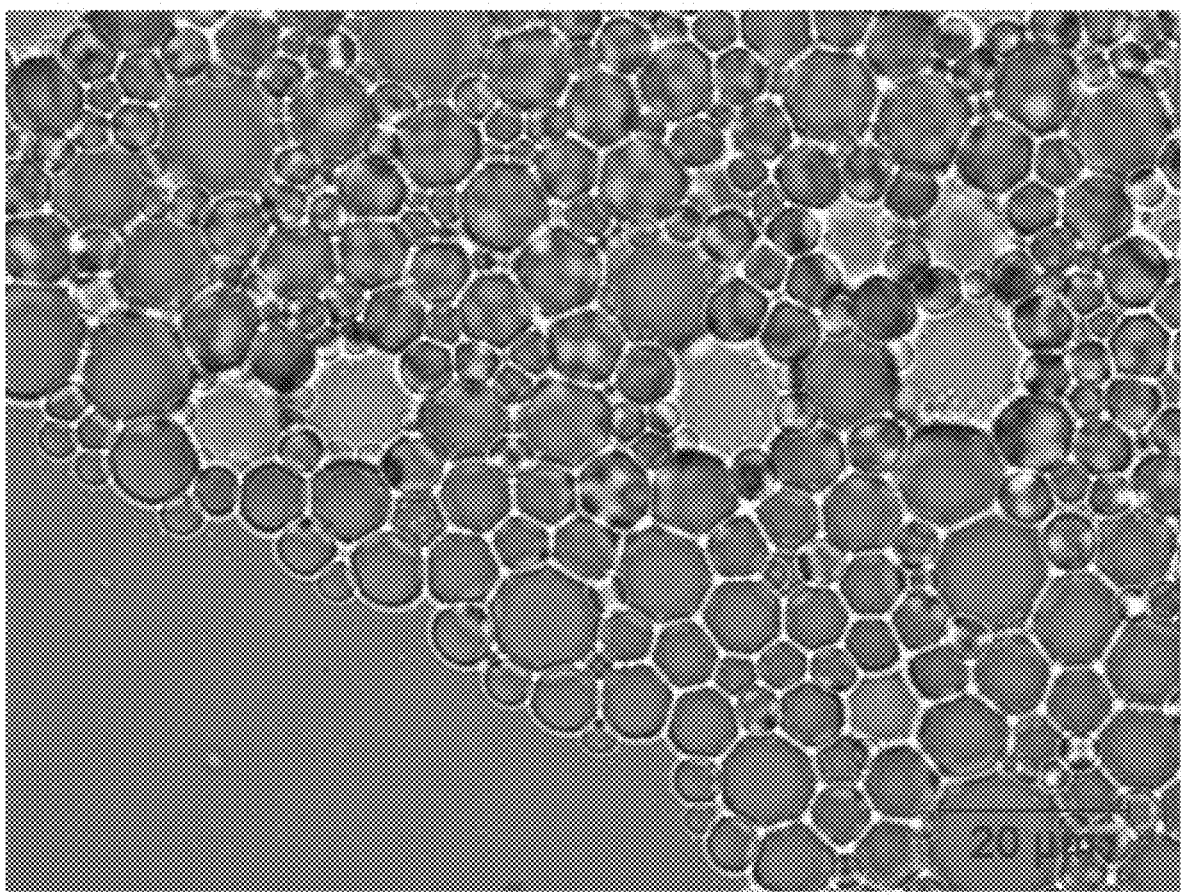

[FIG. 7]
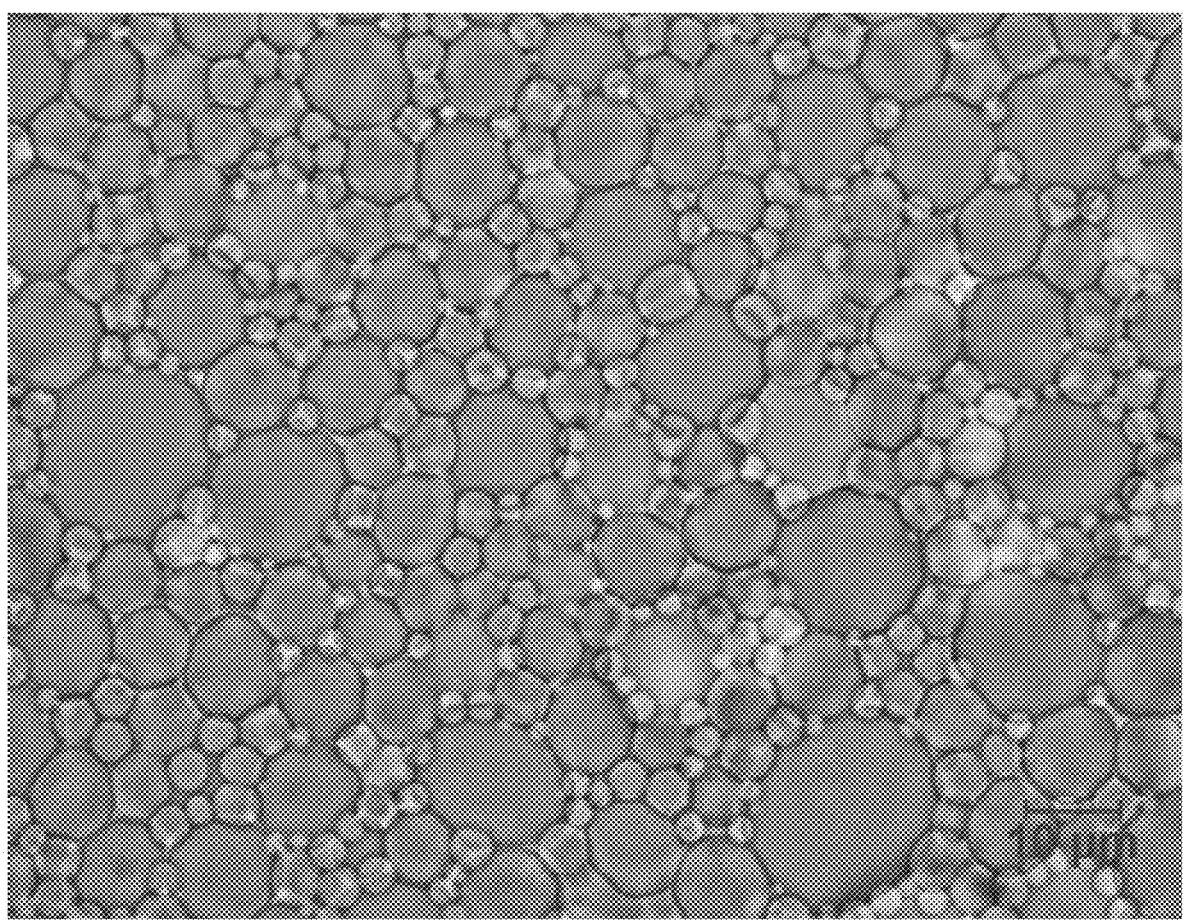

[FIG. 8]
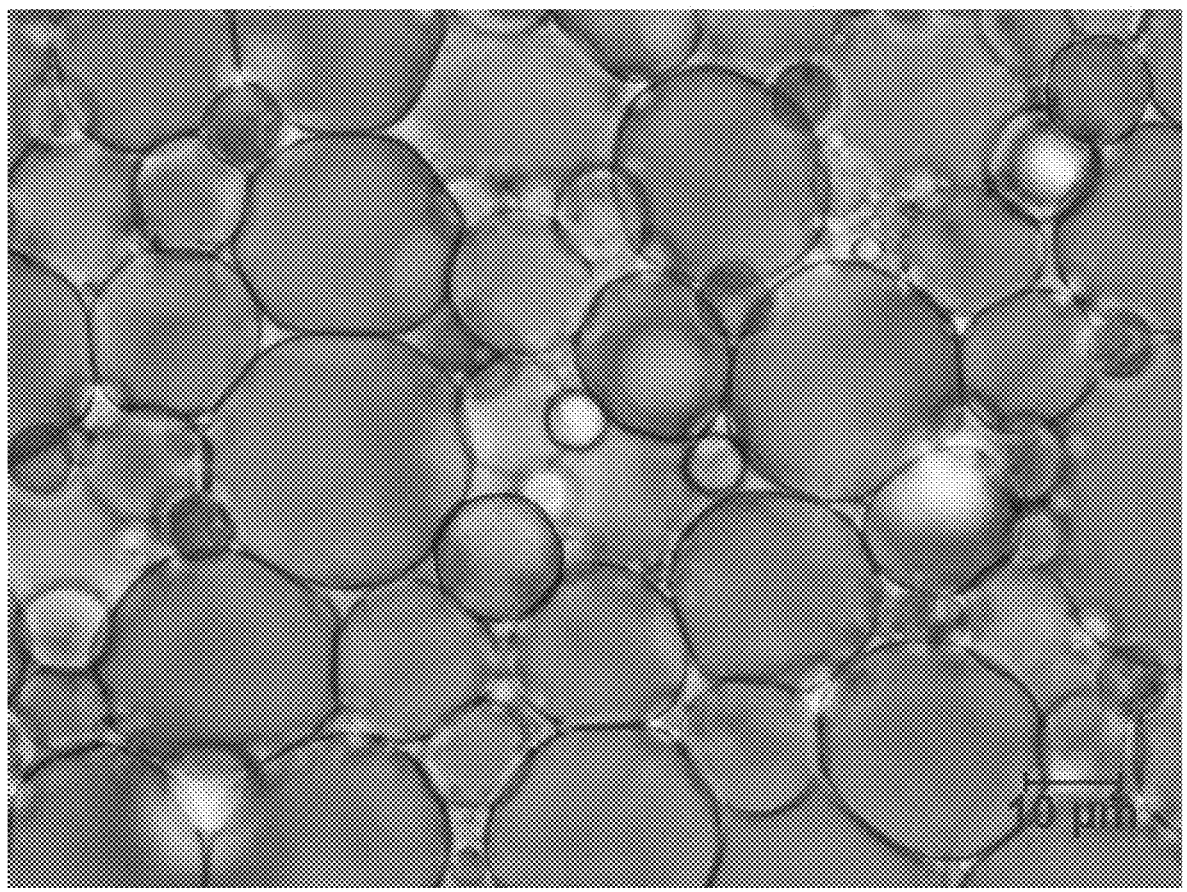

SURFACTANT-FREE COSMETIC COMPOSITION

CROSS-REFERENCE TO RELATED APPLICATION

This application claims under 35 U.S.C. § 119(a) the benefit of Korean Patent Application No. 10-2019-0075350 filed on Jun. 25, 2019, the entire contents of which are incorporated herein by reference.

BACKGROUND

(a) Technical Field

The present invention relates to a surfactant-free cosmetic composition of a water in silicone oil (W/S) formulation containing a stable and high internal phase, while containing a large amount of water-soluble ingredients.

More specifically, the present invention relates to a surfactant-free cosmetic composition capable of maintaining a stable water in silicone oil (W/S) formulation even under prolonged severe conditions, by properly adjusting the content ratio of the emollient having a pyrrolidone carboxylic acid group and the oil-absorbing powder in the composition of the cosmetic composition to stabilize the aqueous phase portion without containing a surfactant.

In addition, the present invention relates to a surfactant-free cosmetic composition capable of maintaining a stable water in silicone oil (W/S) formulation even under prolonged severe conditions, by properly adjusting the weight ratio of the total amount of the emollient having a pyrrolidone carboxylic acid group and the oil-absorbing powder, and the weight of silicone oil in the composition of the cosmetic composition to stabilize the aqueous phase portion without containing a surfactant.

In addition, the present invention relates to a cosmetic composition of a water in silicone oil (W/S) formulation containing a high content of vitamin C or vitamin C derivatives without containing a surfactant, wherein decomposition by the oxidation of the vitamin C or vitamin C derivatives is suppressed, and thus even when stored for a long period of time, its activity does not decrease.

More specifically, the present invention relates to a cosmetic composition of a water in silicone oil (W/S) formulation that stabilizes the aqueous phase portion containing vitamin C or vitamin C derivatives to prevent the vitamin C or vitamin C derivatives from being in contact with the external environment and inhibits decomposition by the oxidation of vitamin C or vitamin C derivatives and thus does not degrade its activity even when stored for a long period of time, by properly adjusting the weight ratio of emollient having a pyrrolidone carboxylic acid group and oil-absorbing powder among the components of cosmetic composition, without containing a surfactant.

(b) Background Art

Typically, the form of cosmetic composition is largely divided into an oil-in-water (O/W) formulation in which the continuous phase is a water-soluble component and a water in oil (W/O) formulation in which the continuous phase is an oil-soluble component. In the case of the oil-in-water (O/W) formulation, the hydrophilic component is preferentially applied to the skin, resulting in a moist and soft feeling of use, whereas in the case of the water-in-oil (W/O) formulation, the oil comes into contact with the skin first, resulting in a heavy oily feeling of use. In order to improve the heavy oily feeling of use, research has been conducted to apply soft and light silicone oils as the continuous phase of the water in oil formulation. Currently, a water in silicone oil (W/S) formulation in which a large amount of silicone oil is used as the outer phase has been developed and delivered to consumers in various products.

These silicone oils are raw materials that are very light and excellent in spreadability and applicability and excellent in safety for the skin due to their unique structural characteristics. In addition, since the silicone oil has a unique appearance and feeling of use depending on the difference in molecular weight and structure, when applied into a formulation, it is possible to form the formulation with a unique shape and impart feeling of use, and thus the water in oil formulation has rapidly developed into a form of water in silicone oil.

On the other hand, a formulation of a high internal-phase water in silicone oil (W/S) generally containing more than 70% of water-soluble components is also a special form of formulation that reflects the unique nature of the silicone described above well. Such a formulation is a unique form of formulation that allows to experience the feeling of use of water burst, since a large amount of aqueous phase portion trapped in the internal phase bursts out as compared to other existing water in silicone oil (W/S) formulations with a large amount of oil phase portion, when applied to the skin. Since such a formulation is a formulation that exhibits coolness and moistness reversely due to the bursting aqueous phase portion, many studies have been conducted, and a preparing technology of high internal-phase macro-emulsion that dramatically increases the amount of aqueous phase portion and emulsifies as much aqueous phase portion as possible in a small amount of silicone oil is becoming a new technology.

However, in the case of the cosmetic composition of the water in silicone oil (W/S) formulation containing the aqueous phase portion of the conventional high internal-phase, the formulation contains surfactants such as PEG or polyglyceryl such as lauryl polyglyceryl-3-polydimethylsiloxyethyl dimethicone, lauryl PEG-9-polydimethylsiloxyethyl dimethicone, and PEG-10 dimethicone as an essential component and is increasing its stability by adding salt to the aqueous phase portion or using an inorganic thickener, but in this case, there is a problem that skin irritation may be caused due to the use of the surfactant, and also it is still difficult to commercialize because stability in prolonged severe conditions of the water in silicone oil (W/S) formulation cannot be expected.

Therefore, in the cosmetic composition of a water in silicone oil (W/S) formulation, the inventors of the present invention have been found that by using an appropriate proportion and content of an emollient having a pyrrolidone carboxylic acid group, oil-absorbing powder and silicone oil in the silicone oil phase portion, even if a surfactant is not included, the over-time stability of the water in silicone oil (W/S) formulation is improved, and when the surfactant-free cosmetic composition is applied to the skin, the high content of the aqueous phase present in the internal phase easily bursts out, resulting in a superior feeling of moisture compared to other formulations and preventing a possibility of being irritated by a surfactant, and thus have completed the present invention.

On the other hand, when the skin is exposed to ultraviolet rays, melanin, which determines the skin color of a person, is synthesized and released, thereby causing hyperpigmentation such as blemishes, freckles, and spots and thus resulting in poor cosmetic results. In the synthesis process of melanin, first, tyrosine in the cell is used as a substrate, and an enzyme called tyrosinase produces dopaquinone, and the copolymer melanin is produced from dopaquinone through an automatic oxidation reaction and an enzyme reaction. Therefore, in order to prevent the skin color from becoming black, a method of reducing the melanin synthesis itself by inhibiting some reactions during the melanin production process has been generally studied. Representative whitening materials known to inhibit the synthesis process described above are kojic acid, arbutin, vitamin A, and vitamin C.

In particular, vitamin C (ascorbic acid) enhances the immune function of the human body, and when applied to the skin, promotes the production of collagen, a component of cartilage, capillaries, and muscles, and destroys chemicals caused by UV rays penetrating the skin, thereby serving to prevent skin damage. In addition, vitamin C is an antioxidant that inhibits the action of active oxygen to prevent wrinkles, keep skin healthy, and help treatment of wounded skin tissue, and vitamin C prevents the formation of melanin that fades the skin during the aging process and is known to have excellent anti-aging and whitening effects that prevent the formation of histamine which is known to cause allergic reactions.

However, vitamin C has a structure similar to γ-lactone, and is unstable, and thus has a problem of being easily decomposed by oxidation by reacting sensitively to the external environment such as air, especially oxygen, heat, and light. The oxidation reaction of vitamin C is usually two continuous electron transfer processes, and is known to generate a dihydroascorbate radical that is an oxidation intermediate of vitamin C due to the dissociation of hydrogen ions, which is rich in reactivity and reacts in itself as 2 molecules and thus produces one molecule of vitamin C and dihydroascorbic acid. Although such vitamin C is dissolved in a very small amount in the non-aqueous solution, a large amount is dissolved in an aqueous solution, but a sufficient amount of vitamin C cannot be stabilized due to the rapid oxidative action of vitamin C. Accordingly, it has been reported that only a small amount of vitamin C can be used as an active ingredient in medicine, food, and cosmetics.

In order to compensate for the problems inherent in vitamin C and improve its stability, studies are continuing to improve the oxidation resistance to water, light and air by using vitamin C derivatives (ascorbic acid derivatives) produced by changing the structure of vitamin C. However, even if the vitamin C derivatives are used, the problem of reduced activity in the formulation still occurs due to the instability of vitamin C itself, and in particular, when using a high content of vitamin C or vitamin C derivatives, this problem becomes even greater.

In order to solve these problems, methods for preventing the degradation of the activity of vitamin C by capturing vitamin C or vitamin C derivatives into the internal phase of the water in oil formulation, and thus blocking vitamin C or vitamin C derivatives from contact with the external environment, such as air, moisture, heat, light, etc. are being studied. In particular, studies to apply soft and light silicone oils as a continuous phase of the water in oil formulation have been conducted to improve the heavy feeling of use of the oil in the water in oil formulation. Currently, a water in silicone oil (W/S) formulation in which a large amount of silicone oil is used as the outer phase has been developed and delivered to consumers in various products.

However, in the case of the conventional cosmetic composition of the water in silicone oil (W/S) formulation comprising the aqueous phase portion of the high internal phase, since a surfactant such as PEG or polyglyceryl such as lauryl polyglyceryl-3-polydimethylsiloxyethyl dimethicone, lauryl PEG-9-polydimethylsiloxyethyl dimethicone, PEG-10 dimethicone, etc. is contained as an essential composition, salt is added to the aqueous phase portion or an inorganic thickener is used, the stability of the formulation can be increased. However, in this case, not only there is a problem that skin irritation may be caused by the use of the surfactant, but also it is still impossible to expect stability of the water in silicone oil (W/S) formulation under severe conditions for a long period of time, which is making it difficult to commercialize. Also, in the case of vitamin C or vitamin C derivatives, it is stable at low pH, so it is desirable to keep the pH of the aqueous phase portion of the water in silicone oil (W/S) formulation low. However, in the case of the conventional water in silicone oil (W/S) formulation, since a thickener such as carbomer sensitive to pH is used, there was a problem in stabilizing vitamin C or vitamin C derivatives.

Therefore, the inventors of the present invention have found that in the cosmetic composition of the water in silicone oil (W/S) formulation containing vitamin C or vitamin C derivatives, the stability over time of the water in silicone oil (W/S) formulation, even without containing a surfactant, can be improved by using an appropriate ratio and content of an emollient having a pyrrolidone carboxylic acid group, an oil-absorbing powder and silicone oil as a portion of the silicone oil phase, and also the stability of the water in silicone oil (W/S) formulation is excellent even at low pH by not using a pH-sensitive thickener, and thus vitamin C or vitamin C derivatives contained in the aqueous phase portion of the water in silicone oil (W/S) formulation can be more stabilized, and have completed the present invention.

PRIOR ART DOCUMENTS

Patent Documents (Patent Document 1) Korean Laid-open Patent Publication No. 10-2019-0046740, "COSMETIC COMPOSITION IN THE FORM OF HIGH INTERNAL PHASE WATER IN SILICONE FORMULATION WITH EXCELLENT STABILITY"

(Patent Document 2) Korean Registered Patent No. 10-1908347, "CHEMICALLY ANISOTROPIC PARTICLES AND W/O EMULSION COMPOSITION COMPRISING THE SAME"

(Patent Document 3) Korean Laid-open Patent Publication No. 10-2007-0079166, "Skin whitening cosmetic compositions containing vitamin C or derivatives thereof"

(Patent Document 4) Korean Laid-open Patent Publication No. 10-2019-0013007, "A COMPOSITION FOR STABILIZING COMPONENT WITH PH SENSITIVITY"

The above information disclosed in this Background section is only for enhancement of understanding of the background of the invention and therefore it may contain information that does not form the prior art that is already known in this country to a person of ordinary skill in the art.

SUMMARY OF THE DISCLOSURE

Therefore, it is an object of the present invention to provide a surfactant-free cosmetic composition capable of stably forming a water in silicone oil (W/S) formulation without containing a surfactant.

In addition, it is another object of the present invention to provide a surfactant-free cosmetic composition that maintains the over-time stability of a water in silicone oil (W/S) formulation even when being stored for a long period of time at high and low temperature conditions, without containing a surfactant.

In addition, it is another object of the present invention to provide a cosmetic composition of a surfactant-free formulation that inhibits decomposition by the oxidation of the vitamin C or vitamin C derivatives and does not degrade its activity when stored for a long period of time, even while containing high content of vitamin C or vitamin C derivatives.

In addition, it is still another object of the present invention to provide a cosmetic composition of a surfactant-free formulation that not only stably forms a water in silicone oil (W/S) formulation containing high content of vitamin C or vitamin C derivatives, but also can maintain the stability over time of the water in silicone oil (W/S) formulation even when stored for a long period of time at high temperature and low temperature conditions, and does not degrade the activity of vitamin C or vitamin C derivatives, without containing a surfactant.

In order to achieve the above objects, the present invention provides a surfactant-free cosmetic composition which is a water in silicone oil (W/S) formulation comprising a silicone oil phase portion and an aqueous phase portion, wherein the silicone oil phase portion contains emollient having a pyrrolidone carboxylic acid group, oil-absorbing powder and silicone oil, and the aqueous phase portion contains water.

In addition, the present invention provides a surfactant-free cosmetic composition wherein the emollient having the pyrrolidone carboxylic acid group is PCA dimethicone.

In addition, the present invention provides a surfactant-free cosmetic composition, wherein the oil-absorbing powder is at least one selected from the group consisting of vinyl dimethicone/methicone silsesquioxane cross-polymer, POLYSILICONE-11, POLYSILICONE-13, diphenyl dimethicone/vinyl diphenyl dimethicone/silsesquioxane cross-polymer, dimethicone/vinyl dimethicone cross-polymer, dimethicone/phenylvinyl dimethicone cross-polymer, and polymethyl silsesquioxane.

In addition, the present invention provides a surfactant-free cosmetic composition, wherein the silicone oil is at least one selected from the group consisting of methicone-based silicone oil, dimethicone-based silicone oil, cyclomethicone-based silicone oil, and phenyl trimethicone-based silicone oil.

In addition, the present invention provides a surfactant-free cosmetic composition wherein the aqueous phase portion contains 20 wt. % or more and 90 wt. % or less of water based on the total weight of the surfactant-free cosmetic composition.

In addition, the present invention provides a surfactant-free cosmetic composition wherein the aqueous phase portion contains 50 wt. % or more and 75 wt. % or less of water based on the total weight of the surfactant-free cosmetic composition.

In addition, the present invention provides a surfactant-free cosmetic composition which has the content of the aqueous phase portion of 30 wt. % or more and 90 wt. % or less based on the total weight of the surfactant-free cosmetic composition.

In addition, the present invention provides a surfactant-free cosmetic composition which has the content of the aqueous phase portion of 75 wt. % or more and 83 wt. % or less based on the total weight of the surfactant-free cosmetic composition.

In addition, the present invention provides a surfactant-free cosmetic composition which has the content of the aqueous phase portion of 79 wt. % or more and 82 wt. % or less based on the total weight of the surfactant-free cosmetic composition.

In addition, the present invention provides a surfactant-free cosmetic composition which has the content ratio of emollient having the pyrrolidone carboxylic acid group and oil-absorbing powder of 1.5:1 to 1:1.5.

In addition, the present invention provides a surfactant-free cosmetic composition which has the content ratio of emollient having the pyrrolidone carboxylic acid group and oil-absorbing powder of 1.5:1 to 3:4.

In addition, the present invention provides a surfactant-free cosmetic composition, wherein the content of emollient and oil-absorbing powder having the pyrrolidone carboxylic acid group is 2 wt. % or more and 6 wt. % or less, respectively, based on the total weight of the surfactant-free cosmetic composition.

In addition, the present invention provides a surfactant-free cosmetic composition, wherein the content of emollient and oil-absorbing powder having the pyrrolidone carboxylic acid group is 3 wt. % or more and 6 wt. % or less, respectively, based on the total weight of the surfactant-free cosmetic composition.

In addition, the present invention provides a surfactant-free cosmetic composition wherein the ratio of the total amount of emollient having the pyrrolidone carboxylic acid group and oil-absorbing powder and the amount of silicone oil is 10:11 to 7:11.

In addition, the present invention provides a surfactant-free cosmetic composition wherein the aqueous phase portion comprises at least one selected from the group consisting of EDTA, ethyl hexyl glycerin, and 1,2-hexanediol.

In addition, the present invention provides a surfactant-free cosmetic composition wherein the viscosity after storage at 45° C. or −15° C. for 4 weeks is 15000 to 30000 cps.

In addition, the present invention provides a surfactant-free cosmetic composition wherein the viscosity after storage at 45° C. or −15° C. for 4 weeks is 20200 to 25000 cps.

In addition, the present invention provides a cosmetic composition of a surfactant-free formulation, wherein the aqueous phase portion further comprises vitamin C or vitamin C derivatives and a pH adjusting agent, the aqueous phase portion is composed of a plurality of particles, and the particles comprise particles having a longest radius of 2.5 to 10 μm.

In addition, the present invention provides a cosmetic composition of a surfactant-free formulation, wherein the silicone oil phase portion further comprises an ester-based oil.

In addition, the present invention provides a cosmetic composition of a surfactant-free formulation, wherein the ester-based oil is at least one selected from the group consisting of ethylhexyl isononanoate, myristyl lactate, cetyl octanoate, ethylhexyl isopalmitate, ethylhexyl isostearate, ethylhexyl myristate, isopropylmyristate, isopropyl palmitate, isocetylethyl hexanoate, octyldodecyl myristate, octyldodecyl stearoyl stearate, ethyl hexyl neopentanoate, ethyl hexyl oleate, ethyl hexyl palmitate, ethyl hexyl stearate, isononyl isononanoate, polyglyceryl-2 triisostearate, pentaerythrityl tetraisostearate, pentaerythrityl tetraethyl hexanoate, cetylethyl hexanoate, diisostearyl malate, caprylic/capric triglyceride, dicaprylyl carbonate, neopentyl glycol dicaprate, butylene glycol dicaprylate/caprate, hexyllaurate, glyceryl triethyl hexanoate, and diglyceryl triisostearate.

In addition, the present invention provides a cosmetic composition of a surfactant-free formulation, wherein the vitamin C derivative is at least one selected from the group consisting of sodium ascorbyl phosphate (SAP), magnesium ascorbyl phosphate (MAP), calcium ascorbyl phosphate, ascorbic acid polypeptide, 3-O-ethyl ascorbic acid, ascorbyl dipalmitate, ascorbyl palmitate, ascorbyl stearate, ascorbyl glucoside, and ascorbyl ethylsilanol pectinate.

In addition, the present invention provides a cosmetic composition of a surfactant-free formulation, wherein the pH adjusting agent is at least one selected from the group consisting of malic acid, citric acid, acetic acid, propionic acid, oxalic acid, glycolic acid, malonic acid, lactic acid, succinic acid, tartaric acid, aspartic acid, maleic acid, glutaric acid, glutamic acid, gluconic acid, sorbic acid, benzoic acid, ascorbic acid, and salicylic acid.

In addition, the present invention provides a cosmetic composition of a surfactant-free formulation, wherein the aqueous phase portion further comprises niacinamide and caffeine.

In addition, the present invention provides a cosmetic composition of a surfactant-free formulation, wherein the aqueous phase portion has a pH of 3.0 to 4.0.

In addition, the present invention provides a cosmetic composition of a surfactant-free formulation, wherein the aqueous phase portion contains 50% or more of particles having a shape satisfying the following equation within a range of 0.1 mm×0.1 mm:

$$0.8 \times (a+b) > a'+b' > 0.95 \times (a+b)$$

wherein a refers to the longest radius of one particle,
b refers to the longest radius of the particle adjacent to the above particle,
a' refers to the distance from the center of gravity of one particle to the outermost point on a straight line connecting the center of gravity of the above particle and the center of gravity of the adjacent particle, and
b' refers to the distance from the center of gravity of the adjacent particle to the outermost point on a straight line connecting the center of gravity of the above particle and the center of gravity of the adjacent particle.

In addition, the present invention provides a cosmetic composition of a surfactant-free formulation, wherein the aqueous phase portion contains 100 or more particles having a longest radius of 5 μm or more within the range of 0.1 mm×0.1 mm.

In addition, the present invention provides a cosmetic composition of a surfactant-free formulation, wherein the pH of the total cosmetic composition of the water in silicone oil (W/S) formulation is 4.3 to 5.0.

In addition, the present invention provides a cosmetic composition of a surfactant-free formulation, wherein the content of vitamin C or vitamin C derivatives is 10 wt. % or more based on the total weight of the cosmetic composition.

According to the present invention, since the cosmetic composition comprises a silicone oil phase portion containing an emollient having a pyrrolidone carboxylic acid group, oil-absorbing powder and silicone oil, and an aqueous phase portion containing water, even if a surfactant is not used, the water in silicone oil (W/S) formulation can be stably formed, and the over-time stability of the water in silicone oil (W/S) formulation can be maintained even when being stored for a long time under conditions of high temperature and low temperature.

In addition, when the cosmetic composition of the present invention is applied to the skin, the high content of water present in the internal phase easily bursts, and thus the feeling of moisture is superior to other water in oil formulations, and since it does not contain a surfactant, irritation and damage to the skin caused by the surfactant can be prevented.

In addition, according to the cosmetic composition of the present invention, even if it contains a high content of vitamin C or vitamin C derivatives, a water in silicone oil (W/S) formulation can be stably formed, and even if it is stored for a long time under conditions of high and low temperature, the stability over time of the water in silicone oil (W/S) formulation may be maintained, and also decomposition by the oxidation of vitamin C or vitamin C derivatives contained in the water in silicone oil (W/S) formulation may be suppressed, thereby preventing the activity from being deteriorated even when stored for a long time.

In addition, the cosmetic composition of the present invention can stably form a water in silicone oil (W/S) formulation even while maintaining a low pH, thereby securing the stability of vitamin C or vitamin C derivatives contained in the water in silicone oil (W/S) formulation.

In addition, when the cosmetic composition of the present invention is applied to the skin, since the high content of water present in the internal phase easily bursts out, the feeling of moisture is superior to that of other water-in-oil formulations, and since a surfactant is not contained, skin irritation and damage caused by the surfactant can be prevented.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention.

FIG. 1 shows a photograph of particles of a surfactant-free cosmetic composition according to Example 1-2 of the present invention. Referring to FIG. 1, it can be seen that due to the aqueous phase portion of the high internal-phase, the emulsion particles form a polygonal shape.

FIG. 2 shows a photograph of the appearance of the surfactant-free cosmetic composition according to Example 1-2 of the present invention, Comparative Examples 1-2 and 1-5. Referring to FIG. 2, it can be seen that the surfactant-free cosmetic composition according to Example 1-2 of the present invention forms a stable water in silicone oil (W/S) formulation, whereas in the case of Comparative Example 1-2, a complete water in silicone oil (W/S) formulation is not formed, and in the case of Comparative Example 1-5, no water in silicone oil (W/S) formulation was formed.

FIG. 3 shows an image comparing appearances after storing the cosmetic composition of the water in silicone oil (W/S) formulation according to Example 2-1 of the present invention and the cosmetic composition of the water in silicone oil (W/S) formulation according to Comparative Example 2-2 at 45° C. for 12 weeks.

FIG. 4 shows an optical microscope (Nikon ECLIPSE LV100POL) image showing particles of the cosmetic composition of the water in silicone oil (W/S) formulation according to Example 2-1 of the present invention (×400 times).

FIG. 5 shows an optical microscope (Nikon ECLIPSE LV100POL) image showing particles of the cosmetic composition of the water in silicone oil (W/S) formulation according to Comparative Example 2-1 of the present invention (×400 times).

FIG. 6 shows an optical microscope (Nikon ECLIPSE LV100POL) image showing particles of the cosmetic composition of the water in silicone oil (W/S) formulation according to Example 2-2 of the present invention (×400 times).

FIG. 7 shows an optical microscope (Nikon ECLIPSE LV100POL) image showing particles of the cosmetic composition of the water in silicone oil (W/S) formulation according to Example 2-6 of the present invention (×1000 times).

FIG. 8 shows an optical microscope (Nikon ECLIPSE LV100POL) image showing particles of the cosmetic composition of the water in silicone oil (W/S) formulation according to Example 2-7 of the present invention (×1000 times).

It should be understood that the appended drawings are not necessarily to scale, presenting a somewhat simplified representation of various preferred features illustrative of the basic principles of the invention.

DETAILED DESCRIPTION

Hereinafter, in order to enable those skilled in the art to which the present invention pertains to easily implement the present invention, preferred embodiments of the present invention will be described in detail.

The cosmetic composition of the water in silicone oil (W/S) formulation mentioned in the present invention means a cosmetic composition composed of an aqueous phase portion dispersed in an external silicone oil phase portion which is a continuous phase. In addition, the surfactant-free cosmetic composition referred to in the present invention means a cosmetic composition of a water in silicone oil (W/S) formulation containing 0.1 wt. % or less of a surfactant.

The surfactant-free cosmetic composition according to the present invention is a water in silicone oil (W/S) formulation comprising a silicone oil phase portion and an aqueous phase portion, wherein the silicone oil phase portion may comprise emollient having a pyrrolidone carboxylic acid group, oil-absorbing powder and silicone oil, and the aqueous phase portion may comprise water.

Hereinafter, the composition of the surfactant-free cosmetic composition of the present invention will be described in more detail.

First, the surfactant-free cosmetic composition of the present invention may be a water in silicone oil (W/S) formulation composed of an outer phase consisting of an oil phase portion and an internal phase consisting of an aqueous phase portion.

The silicone oil phase portion of the surfactant-free cosmetic composition of the present invention may comprise emollient having a pyrrolidone carboxylic acid group, oil-absorbing powder and silicone oil.

The emollient having the pyrrolidone carboxylic acid group may be selected from PCA dimethicone and amodimethicone, and the oil-absorbing powder may be silicone powder, specifically, at least one selected from the group consisting of vinyl dimethicone/methicone silsesquioxane cross-polymer, POLYSILICONE-11, POLYSILICONE-13, diphenyl dimethicone/vinyl diphenyl dimethicone/silsesquioxane cross-polymer, dimethicone/vinyl dimethicone cross-polymer, dimethicone/phenylvinyl dimethicone cross-polymer and polymethylsilsesquioxane, and may preferably be vinyl dimethicone/methicone silsesquioxane cross-polymer.

In the present invention, the emollient having the pyrrolidone carboxylic acid group and oil-absorbing powder can act as a bulking agent in the manufacture of cosmetics. For this reason, the cosmetic composition of the present invention is capable of maintaining a stable water in silicone oil (W/S) formulation even under severe conditions of high temperature and low temperature for a long period of time, by stabilizing the aqueous phase portion of the high internal-phase even if it does not contain a surfactant.

In addition, the silicone oil may be at least one selected from the group consisting of methicone-based silicone oil, dimethicone-based silicone oil, cyclomethicone-based silicone oil and phenyl trimethicone-based silicone oil, and may preferably be phenyl trimethicone-based silicone.

The content of the oil phase portion may be 10 wt. % or more and 70 wt. % or less, preferably 15 wt. % or more and 30 wt. % or less, more preferably 17 wt. % or more and 21 wt. % or less, even more preferably 18 wt. % or more and 21 wt. % or less, based on the total weight of the surfactant-free cosmetic composition. If the content of the oil phase portion is less than 10 wt. %, the content of the outer phase is too small to stably form the formulation. If the content of the oil phase portion is more than 70 wt. %, it is not preferable because stability and feeling of use of the formulation are lowered.

The aqueous phase portion of the surfactant-free cosmetic composition of the present invention may contain 20 wt. % or more and 90 wt. % or less of water, preferably 50 wt. % or more and 75 wt. % or less of water, more preferably 51 wt. % or more and 60 wt. % or less of water, even more preferably 52.9 wt. % or more and 55.9 wt. % or less of water, based on the total weight of the surfactant-free cosmetic composition. If the content of water is less than 50 wt. %, the content of the internal phase is too small to provide sufficient feeling of moisture. If the content of water is more than 90 wt. %, it is not preferable because it is difficult to stably form the formulation.

In addition, the content of the aqueous phase portion in the surfactant-free cosmetic composition of the present invention may be 30 wt. % or more and 90 wt. % or less, preferably 70 wt. % or more and 85 wt. % or less, more preferably 75 wt. % or more and 83 wt. % or less, even more preferably 79 wt. % or more and 82 wt. % or less, based on the total weight of the surfactant-free cosmetic composition. If the content of the aqueous phase portion is less than 30 wt. %, the content of the internal phase is too small to provide sufficient feeling of moisture. If the content of the aqueous phase portion is more than 90 wt. %, it is not preferable because it is difficult to stably form the formulation.

The content ratio of the emollient having the pyrrolidone carboxylic acid group and the oil-absorbing powder in the surfactant-free cosmetic composition of the present invention may be 2:1 to 1:2, preferably 1.5:1 to 1:1.5, more preferably 1.5:1 to 3:4. If the content ratio of the emollient having the pyrrolidone carboxylic acid group and the oil-absorbing powder is outside the above range, the water in silicone oil (W/S) formulation is not completely formed or the water in silicone oil (W/S) formulation is not maintained for a long period of storage, which is undesirable.

In addition, each of the emollient having the pyrrolidone carboxylic acid group and the oil-absorbing powder in the surfactant-free cosmetic composition of the present invention may be 2 wt. % or more and 6 wt. % or less, preferably more than 2 wt. % and 6 wt. % or less, more preferably 3 wt. % or more and 5 wt. % or less, based on the total weight of the surfactant-free cosmetic composition. If the content of each of the emollient having the pyrrolidone carboxylic acid group and the oil-absorbing powder is outside the above range, the water in silicone oil (W/S) formulation is not maintained during long-term storage, which is not preferable.

In addition, the ratio of the total amount of emollient having the pyrrolidone carboxylic acid group and oil-absorbing powder and the amount of silicone oil in the surfactant-free cosmetic composition of the present invention may be 1:1 to 4:11, preferably 10:11 to 4:11, more preferably 10:11 to 7:11. If the ratio of the total amount of emollient having the pyrrolidone carboxylic acid group and oil-absorbing powder and the amount of silicone oil is outside the above range, the water in silicone oil (W/S) formulation is not maintained during long-term storage, which is not preferable.

The aqueous phase portion of the surfactant-free cosmetic composition of the present invention may include water and other additives. More specifically, the aqueous phase portion may be, but is not limited to, at least one selected from the group consisting of water, and polyols such as glycerin, propanediol, 1,2-hexanediol, butylene glycol, and caprylyl glycol, various emollients and humectants such as sodium chloride, EDTA, water-soluble functional raw materials (arbutin, niacin amide, adenosine, etc.), and ethyl hexyl glycerin and the like. The aqueous phase portion may be used differently depending on the feeling of use and functionality of the composition. Preferably, the aqueous phase portion may further comprise at least one selected from the group consisting of EDTA, ethyl hexyl glycerin, and 1,2-hexanediol.

The aqueous phase portion of the cosmetic composition of the surfactant-free formulation of the present invention may further comprise vitamin C or vitamin C derivatives and a pH adjusting agent.

The vitamin C derivatives refer to those in which various molecules are organo-chemically attached to the carbon chain of vitamin C so as not to be easily oxidized in a raw material state or in a dissolved or dispersed state, while maintaining the level of activity that normally appears when the original vitamin C is applied to the skin. These chemically bonded molecules act as steric hindrances that physically protect the double bond between the carbons at positions 2 and 3 of vitamin C from being easily broken by external stimuli.

These vitamin C derivatives may be at least one selected from the group consisting of sodium ascorbyl phosphate (SAP), magnesium ascorbyl phosphate (MAP), calcium ascorbyl phosphate, ascorbic acid polypeptide, 3-O-ethyl ascorbic acid, ascorbyl dipalmitate, ascorbyl palmitate, ascorbyl stearate, ascorbyl glucoside and ascorbyl ethylsilanol pectinate, preferably 3-O-ethyl ascorbic acid.

The aqueous phase portion may comprise a pH adjusting agent to stabilize the vitamin C or vitamin C derivatives, and preferably may comprise an acidic pH adjusting agent.

The pH adjusting agent may be at least one selected from the group consisting of malic acid, citric acid, acetic acid, propionic acid, oxalic acid, glycolic acid, malonic acid, lactic acid, succinic acid, tartaric acid, aspartic acid, maleic acid, glutaric acid, glutamic acid, gluconic acid, sorbic acid, benzoic acid, ascorbic acid and salicylic acid, preferably citric acid, glycolic acid, and salicylic acid, more preferably citric acid. If the aqueous phase portion contains salicylic acid as a pH adjusting agent, the aqueous phase portion may further comprise niacinamide and caffeine to dissolve salicylic acid.

The aqueous phase portion may comprise the pH adjusting agent, so that the pH of the aqueous phase portion is 3.0 to 4.0, preferably 3.6 to 3.8. If the pH of the aqueous phase portion is less than 3.0, there is a risk of irritation to the skin. If the pH of the aqueous phase portion is 4.0 or higher, stability of vitamin C or vitamin C derivatives may be deteriorated. Therefore, it is preferable that the pH of the aqueous phase portion satisfies the above range.

The aqueous phase portion in the cosmetic composition of the surfactant-free formulation of the present invention, which further comprises vitamin C or vitamin C derivatives and a pH adjusting agent, may comprise 45 wt. % or more and 80 wt. % or less of water, preferably 50 wt. % or more and 70 wt. % or less of water, more preferably 55 wt. % or more and 60 wt. % % or less, relative to the total weight of the cosmetic composition of the water in silicone oil (W/S) formulation. If the content of water is less than 45 wt. %, the content of the internal phase is too small, so that the feeling of moisture is insufficient, and vitamin C or vitamin C derivatives are difficult to dissolve sufficiently. If the content of water is more than 80 wt. %, it is not preferable because it is difficult to stably form the formulation.

The content of the aqueous phase portion in the cosmetic composition of the surfactant-free formulation of the present invention, which further comprises vitamin C or vitamin C derivatives and a pH adjusting agent, may be 75 wt. % or more and 90 wt. % or less, preferably 80 wt. % or more and 90 wt. % or less, and more preferably 82 wt. % or more and 86 wt. % or less, relative to the total weight of the cosmetic composition of the surfactant-free formulation. If the content of the aqueous phase portion is less than 75 wt. %, the content of the aqueous phase portion is too small, so that the feeling of moisture is insufficient. If the content of the aqueous phase portion is more than 90 wt. %, it is not preferable because it is difficult to stably form the formulation.

In the aqueous phase portion in the cosmetic composition of the surfactant-free formulation of the present invention which further comprises vitamin C or vitamin C derivatives and a pH adjusting agent, since particles with a large particle size are present at a high density, each particle does not have the shape of a complete circle, but represents the shape of an incomplete circle with some distortion. In addition, the shape of the incomplete circle may be polygonal, specifically, may be pentagonal to decagonal, preferably pentagonal to octagonal.

In addition, the particles included in the aqueous phase portion may satisfy the following equation:

$$0.8 \times (a+b) > a' + b' > 0.95 \times (a+b)$$

wherein a refers to the longest radius of one particle, b refers to the longest radius of the particle adjacent to the above particle, a' refers to the distance from the center of gravity of one particle to the outermost point on a straight line connecting the center of gravity of the above particle and the center of gravity of the adjacent particle, and b' refers to the distance from the center of gravity of the adjacent particle to the outermost point on a straight line connecting the center of gravity of the above particle and the center of gravity of the adjacent particle.

The longest radius of the particle means the longest distance among the distances from the center of gravity of the particle to the outermost point.

In addition, the aqueous phase portion in the cosmetic composition of the surfactant-free formulation of the present invention, which further comprises vitamin C or vitamin C derivatives and a pH adjusting agent, may contain 50% or more, preferably 65% or more, more preferably 80% or more of particles having a shape satisfying the following equation within a range of 0.1 mm×0.1 mm:

$$0.8\times(a+b) > a'+b' > 0.95\times(a+b)$$

wherein a refers to the longest radius of one particle, b refers to the longest radius of the particle adjacent to the above particle, a' refers to the distance from the center of gravity of one particle to the outermost point on a straight line connecting the center of gravity of the above particle and the center of gravity of the adjacent particle, and b' refers to the distance from the center of gravity of the adjacent particle to the outermost point on a straight line connecting the center of gravity of the above particle and the center of gravity of the adjacent particle.

In addition, the aqueous phase portion in the cosmetic composition of the surfactant-free formulation of the present invention, which further comprises vitamin C or vitamin C derivatives and a pH adjusting agent, may contain 50 or more, preferably 80 or more, more preferably 100 or more particles having a size of 5 μm or more in the longest radius within a range of 0.1 mm×0.1 mm.

In the aqueous phase portion in the cosmetic composition of the surfactant-free formulation of the present invention which further comprises vitamin C or vitamin C derivatives and a pH adjusting agent, if the aqueous phase portion contains less than 50% of particles satisfying the above equation or contains less than 50 particles having a longest radius of 5 μm or more, the feeling of use is not good, for example, the feeling of moisture is not sufficient, and the stability of the formulation is not good.

In addition, the pH of the entire cosmetic composition of the surfactant-free formulation of the present invention, which further comprises vitamin C or vitamin C derivatives and a pH adjusting agent, may be 4.3 to 5.0, preferably 4.3 to 4.5. If the pH of the entire cosmetic composition of the surfactant-free formulation of the present invention, which further comprises vitamin C or vitamin C derivatives and a pH adjusting agent, is less than 4.3, there is a risk of irritation to the skin. If the pH is 5.0 or more, the stability of vitamin C or vitamin C derivatives may be deteriorated. Therefore, it is preferable that the pH of the entire cosmetic composition of the surfactant-free formulation of the present invention, which further comprises vitamin C or vitamin C derivatives and a pH adjusting agent, satisfies the above range.

In addition, the cosmetic composition of the surfactant-free formulation of the present invention may contain 10 wt. % or more of vitamin C or vitamin C derivatives. The cosmetic composition of the surfactant-free formulation can inhibit the decomposition by the oxidation of vitamin C or vitamin C derivatives even if it contains more than 10 wt. % of vitamin C or vitamin C derivatives, and prevent the deterioration of activity even after long-term storage.

The aqueous phase portion in the surfactant-free formulation of the present invention may further comprise other additives. More specifically, the aqueous phase portion may contain, but is not limited to, at least one from the group consisting of polyols such as glycerin, propanediol, 1,2-hexanediol, butylene glycol, and caprylyl glycol, sodium chloride, disodium EDTA, water-soluble functional raw materials (arbutin, niacinamide, adenosine, caffeine, etc.), various emollient, such as ethyl hexyl glycerin, and moisturizers, etc. The aqueous phase portion may be used differently depending on the feeling of use and functionality of the composition. Preferably, the aqueous phase portion may further include at least one selected from the group consisting of glycerin, butylene glycol, propanediol, disodium EDTA, ethyl hexyl glycerin and 1,2-hexanediol.

The surfactant-free cosmetic composition of the present invention may have a viscosity of 15000 to 30000 cps even after long-term storage at high and low temperatures. Specifically, the surfactant-free cosmetic composition of the present invention may have a viscosity of 15000 to 30000 cps, preferably 20000 to 25000 cps, more preferably 20200 to 25000 cps even after storing at 45° C. and −15° C. for 4 weeks. That is, the surfactant-free cosmetic composition of the present invention can stably maintain a water in silicone oil (W/S) formulation even after long-term storage at high and low temperatures.

The cosmetic composition of the surfactant-free formulation of the present invention may contain a surfactant in an amount of 0.1 wt. % or less, and preferably may not contain a surfactant. If the content of the surfactant is outside the above range, since there is a problem that skin irritation may be caused by the use of the surfactant, it is preferable to contain the surfactant within the above range.

Hereinafter, the present invention will be described in more detail through examples. The following examples are only presented by way of example to describe the present invention in more detail, and it will be apparent to those skilled in the art that the scope of the present invention is not to be construed as limited by these examples.

Example 1: Preparation of Cosmetic Composition of Water in Silicone Oil (W/S) Formulation Cosmetic compositions of the water in silicone oil (W/S) formulations of Examples 1-1 to 1-4 and Comparative Examples 1-1 to 1-6 having the composition of Table 1 below were prepared.

Specifically, an emollient having a pyrrolidone carboxylic acid group, oil-absorbing powder, and silicone oil were added into a polyol, and the mixture was stirred slowly at a low speed of 100 rpm for 2 minutes, using a paddle mixer (Manufacturer: GLOBAL LAB, Model name: SS-20 DIRECT DRIVEN STIRRER). To the resulting mixture, water and other additives were slowly added and stirred for 5 minutes at a speed of 100 rpm using a paddle mixer to prepare a cosmetic composition of a water in silicone oil (W/S) formulation.

Glycerin and propanediol (=10:15) were used as the polyol, and PCA dimethicone (Manufacturer: CRODA, Product name: SENSASIL-PCA-LQ, Acid value: 10 mg KOH/g) was used as the emollient having the pyrrolidone carboxylic acid group, and phenyl trimethicone (Manufacturer: ShinEtsu, Raw material: TMF-1.5, Viscosity: 1.4-1.9 cps, or Manufacturer: DOW CORNING, Raw material: UP-556 FLUID, Viscosity: 15-30 cps) was used as the silicone oil, and vinyl dimethicone/methicone silsesquioxane cross-polymer (Manufacturer: ShinEtsu, Raw material: KSP-101, average particle size: 13 μm) was used as the oil-absorbing powder. In addition, EDTA, ethyl hexyl glycerin, and 1,2-hexanediol were used as the other additives.

The detailed composition of the surfactant-free cosmetic composition prepared according to the above is shown in Table 1 below.

TABLE 1

|  | Example 1-1 | Example 1-2 | Example 1-3 | Example 1-4 | Comparative Example 1-1 | Comparative Example 1-2 | Comparative Example 1-3 | Comparative Example 1-4 | Comparative Example 1-5 | Comparative Example 1-6 |
|---|---|---|---|---|---|---|---|---|---|---|
| PCA dimethicone | 3 | 4 | 5 | 6 | 2 | 3 | 2 |  | 4 | 4 |
| Dimethicone |  |  |  |  |  |  |  | 3 |  |  |
| Phenyltrimethicone | 11 | 11 | 11 | 11 | 11 | 11 | 11 | 11 | 11 | 8 |
| Vinyldimethicone/ methiconesilsesquioxane cross-polymer | 4 | 4 | 4 | 4 | 4 | 6 | 2 | 4 |  | 4 |
| Polyol (Glycerin:propanediol = 10:15) | 25 | 25 | 25 | 25 | 25 | 25 | 25 | 25 | 25 | 25 |
| Water | to 100 | to 100 | to 100 | to 100 | to 100 | to 100 | to 100 | to 100 | to 100 | to 100 |
| EDTA | 0.05 | 0.05 | 0.05 | 0.05 | 0.05 | 0.05 | 0.05 | 0.05 | 0.05 | 0.05 |
| Ethyl hexyl glycerin | 0.05 | 0.05 | 0.05 | 0.05 | 0.05 | 0.05 | 0.05 | 0.05 | 0.05 | 0.05 |
| 1,2-Hexanediol | 1 | 1 | 1 | 1 | 1 | 1 | 1 | 1 | 1 | 1 |

\* The unit of each value in the above table represents parts by weight.

Experimental Example 1-1: Measurement of Hardness of Cosmetic Composition of Water in Silicone Oil (W/S) Formulation In order to confirm the stability of the formulation of the cosmetic composition of the water in silicone oil (W/S) formulation, the hardness immediately after preparation of the cosmetic compositions of the water in silicone oil (W/S) formulations of Examples 1-1 to 1-4 and Comparative Examples 1-2 to 1-6 was measured. The hardness measurement was performed using a hardness meter (Manufacturer: Sun scientific Co. Ltd., Model name: CR-100D, Japan), and the force required to permeate 20 mm into the contents at a rate of 10 mm/min on a sample at 30° C. was measured.

The results are shown in Table 2 below.

TABLE 2

|  | Example 1-1 | Example 1-2 | Example 1-3 | Example 1-4 | Comparative Example 1-2 | Comparative Example 1-3 | Comparative Example 1-4 | Comparative Example 1-5 | Comparative Example 1-6 |
|---|---|---|---|---|---|---|---|---|---|
| Immediately after preparing (Hardness, Room temperature) | 18 | 25 | 20 | 17 | Impossible to form complete W/S | 14 | Impossible to form complete W/S | Impossible to form complete W/S | 36 |

\* The unit of each value in the above table is ($1.0 \times 10^{-3}$ N units).

As a result of the above experiment, it was confirmed that in the case of Examples 1-1 to 1-4, the hardness was 17 to 25 ($1.0 \times 10^{-3}$ N), so that the formulation was stably formed, whereas in the case of Comparative Examples 1-2, 1-4, and 1-5, the formation of a water in silicone oil (W/S) formulation was impossible, and in the case of Comparative Example 1-3, the hardness was 14 ($1.0 \times 10^{-3}$ N), and the content of oil-absorbing powder and PCA dimethicone was insufficient, so that the aqueous phase portion could not be sufficiently stabilized, and in the case of Comparative Example 1-6, the content of the internal phase (aqueous phase portion 84%) was high, and thus the highest hardness of 36 ($1.0 \times 10^{-3}$ N) was shown, but afterward, the aqueous phase portion in the internal phase was leached out and water in silicone oil (W/S) formulation becomes unstable.

In addition, a microscopic particle photograph of the cosmetic composition of the water in silicone oil (W/S) formulation of Example 1-2 having an aqueous phase portion of a high internal phase of 81 wt. % are shown in FIG. 1. Looking at the above FIG. 1, it was confirmed that the distorted emulsion particles due to the high internal-phase have a polygonal shape.

Therefore, it was found that the surfactant-free cosmetic composition according to the present invention is capable of forming a stable water in silicone oil (W/S) formulation.

Experimental Example 1-2: Evaluation of Over-Time Stability of Cosmetic Composition of Water in Silicone Oil (W/S) Formulation In order to confirm the over-time stability of the cosmetic composition of the water in silicone oil (W/S) formulation, the cosmetic compositions of Examples 1-1 to 1-4 and Comparative Examples 1-1, 1-3 and 1-6 were put in a 100 mL PET container, placed in an incubator (Manufacturer: JISICO, Model name: J-100M Incubator), and set the temperature of the incubator to 30° C., and then the viscosity after storage for 24 hours, 1 week, and 4 weeks was measured for 2 minutes at a speed of 12 rpm with 64 spindles using a viscometer (manufacturer: Brookfield, model name: LVDV-II+P).

The results are shown in Table 3 below.

TABLE 3

|  | Example 1-1 | Example 1-2 | Example 1-3 | Example 1-4 | Comparative Example 1-1 | Comparative Example 1-3 | Comparative Example 1-6 |
|---|---|---|---|---|---|---|---|
| 24 hours later (Viscosity, 30° C.) | 22000 | 33000 | 31500 | 29700 | 38600 | 29700 | Water is leached |
| 1 week later (Viscosity, 30° C.) | 21000 | 25000 | 23000 | 20200 | Water is leached | Water is leached | |
| 4 weeks later (Viscosity, 30° C.) | 21000 | 25000 | 23000 | 20200 | | | |

* The unit of viscosity in the above table is cps.

As a result of the experiment, in the case of Examples 1-1 to 1-4, the viscosity was maintained at 20200 to 33000 cps, even after 24 hours, after 1 week and after 4 weeks of storage, and water was not leached and thus a stable lotion and essence type of the water in silicone oil (W/S) formulation was maintained.

On the other hand, in the case of Comparative Example 1-6, it was confirmed that water leached out after 24 hours of storage, and in the case of Comparative Examples 1-1 and 1-3, it was confirmed that water was leached out after one week of storage.

Therefore, it was found that the surfactant-free cosmetic composition according to the present invention maintains a stable water in silicone oil (W/S) formulation at a temperature of 30° C. even after 24 hours, after 1 week and after 4 weeks of storage.

Experimental Example 1-3: Evaluation of the Stability of the Cosmetic Composition of the Water in Silicone Oil (W/S) Formulation Under Heating and Cooling Conditions and Freezing and Thawing Conditions In order to confirm the stability of the cosmetic composition of the water in silicone oil (W/S) formulation under heating and cooling conditions and freezing and thawing conditions, cosmetic compositions having the compositions of Examples 1-1 to 1-4 were evaluated for stability after storage under the following specific conditions.

Specifically, the cosmetic compositions having the compositions of Examples 1-1 to 1-4 were placed in an incubator (Manufacturer: JISICO company, Model name: J-MIC2 Incubator), the temperature was set to 45° C. and then the process of storing for 1 week and then cooling to room temperature was repeated 4 times, and thus for 4 weeks.

In addition, the cosmetic compositions having the compositions of Examples 1-1 to 1-4 were placed in a freezer (Manufacturer: DAEYOUNG ONE CO., LTD., Model name: LD-1140RF), the temperature was set to −15° C., and then the process of storing for 1 week and then thawing to room temperature was repeated 4 times, and thus for 4 weeks.

However, in the case of Comparative Examples 1-1 to 1-6, it was not possible to evaluate the stability because a stable water in silicone oil (W/S) formulation was not formed or the formulation was separated.

The results are shown in Table 4 below.

TABLE 4

|  | Example 1-1 | Example 1-2 | Example 1-3 | Example 1-4 | Comparative Example 1-1 | Comparative Example 1-2 | Comparative Example 1-3 | Comparative Example 1-4 | Comparative Example 1-5 | Comparative Example 1-6 |
|---|---|---|---|---|---|---|---|---|---|---|
| High Temperature (45° C.), after 4 weeks | stable | stable | stable | stable | — | — | — | — | — | — |
| Low temperature (−15° C.), after 4 weeks | stable | stable | stable | stable | — | — | — | — | — | — |

As a result of the above experiment, in the case of Examples 1-1 to 1-4, it was possible to maintain a stable water in silicone oil (W/S) formulation even after being stored for 4 weeks or more under heating and cooling conditions at a high temperature (45° C.) and freezing and thawing conditions at a low temperature (−15° C.), as described above. In addition, if the polyol was 25 wt. % or more, it was confirmed that the water in silicone oil (W/S) formulation was stably maintained because it did not solidify even under the condition of repeated thawing after freezing.

As can be seen through the above Experimental Examples 1-1 to 1-3, in the case of preparing a cosmetic composition of a water in silicone oil (W/S) formulation as in the present invention, it was confirmed that if the PCA dimethicone as an emollient having a pyrrolidone carboxylic acid group and the vinyl dimethicone/methicone silsesquioxane cross-polymer as a oil-absorbing powder were contained in a ratio of 1:1, the viscosity was highest (Example 1-2), and it was confirmed that if the proportion and content of the oil-absorbing powder is increased, the stability is decreased, and if the content of oil-absorbing powder is 6 wt. %, which is twice the content of PCA dimethicone, the aqueous phase portion cannot enter the internal phase entirely, so that a water in silicone oil (W/S) formulation and water coexist (Comparative Example 1-2).

In addition, it was found that if PCA dimethicone as an emollient having a pyrrolidone carboxylic acid group and vinyl dimethicone/methicone silsesquioxane cross-polymer as a oil-absorbing powder are used in a ratio of 1.5:1 to 1:1.5, respectively, in a content of 2 wt. % or more, a cosmetic composition of a stable water in silicone oil (W/S) formulation can be obtained without using a common surfactant.

Therefore, it was found that if the cosmetic composition of the present invention is used, water in silicone oil (W/S) formulation can be stably formed, the over-time stability of the water in silicone oil (W/S) formulation can be maintained even when being stored for a long period of time at high and low temperature conditions.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

Example 2: Preparation of Cosmetic Composition of Water in Silicone Oil (W/S) Formulation Cosmetic compositions of water in silicone oil (W/S) formulations of Examples 2-1 to 2-8 and Comparative Examples 2-1 to 2-6 having composition of Table 5 below were prepared.

Specifically, an emollient having a pyrrolidone carboxylic acid group, an oil-absorbing powder and silicone oil were added in a polyol, and the mixture was sufficiently stirred at room temperature at a rate of 300 rpm, using a paddle mixer (Manufacturer: GLOBAL LAB, Model: SS-20 DIRECT DRIVEN STIRRER). To the obtained mixture, the aqueous part in which water, vitamin C derivatives, a pH adjusting agent and other additives were dissolved was added and at the same time, stirred for 5 minutes at a low speed of 100 rpm or less using a paddle mixer to prepare a cosmetic composition of a water in silicone oil (W/S) formulation.

As the polyol, glycerin, butylene glycol and propanediol were used. As the emollient having a pyrrolidone carboxylic acid group, PCA dimethicone (Manufacturer: CRODA, Product name: SENSASIL-PCA-LQ, Acid value: 10 mg KOH/g) was used. As the silicone oil, phenyl trimethicone (Manufacturer: ShinEtsu, Raw material name: TMF-1.5, Viscosity: 1.4 to 1.9 cps, or Manufacturer: DOW CORNING, Raw material name: UP-556 FLUID, Viscosity: 15 to 30 cps)/caprylyl methicone (Manufacturer: DOW CHEMICAL PACIFIC, Raw material name: DOWSIL™ FZ-3196 Fluid, Viscosity: 2 to 4 cps) was used. As the oil-absorbing powder, vinyl dimethicone/methicone silsesquioxane cross polymer (Manufacturer: ShinEtsu, Raw material name: KSP-101, Average particle size: 13 μm) was used. In addition, pentaerythrityl tetraisostearate was used as the ester-based oil. In addition, 3-O-ethyl ascorbic acid was used as the vitamin C derivative, citric acid and tromethamine were used as the pH adjusting agent, and disodium EDTA, ethyl hexyl glycerin and 1,2-hexandiol were used as the other additives. In addition, CETYL PEG/PPG-10/1DIMETHICONE (ABIL EM 90, EVONIK) was used as surfactant.

The detailed composition of the cosmetic composition of the water in silicone oil (W/S) formulation prepared according to the above is shown in Tables 5-1 and 5-2 below.

TABLE 5-1

| | Component | Example 2-1 | Example 2-2 | Example 2-3 | Example 2-4 | Example 2-5 | Example 2-6 | Example 2-7 | Example 2-8 |
|---|---|---|---|---|---|---|---|---|---|
| Silicone oil phase portion | PCA dimethicone | 3 | 3 | 4 | 5 | 6 | 3 | 3 | 3 |
| | Vinyl dimethicone/Methicone silsesquioxane cross-polymer (oil-absorbing powder) | 4 | 4 | 4 | 4 | 4 | 4 | 4 | 4 |
| | Phenyltrimethicone/caprylylmethicone(silicone oil) | 7 | 7 | 7 | 7 | 7 | 7 | 7 | 7 |
| | Pentaerythrityl tetraisostearate(ester-based oil) | 4 | — | — | — | — | 4 | 4 | 4 |
| Aqueous phase portion | Glycerin | 5 | 5 | 5 | 5 | 5 | 5 | 5 | 5 |
| | Butylene glycol | 5 | 5 | 5 | 5 | 5 | 5 | 5 | 5 |
| | Propanediol | 5 | 5 | 5 | 5 | 5 | 5 | 5 | 5 |
| | Water | to 100 | to 100 | to 100 | to 100 | to 100 | to 100 | to 100 | to 100 |
| | Disodium EDTA | 0.05 | 0.05 | 0.05 | 0.05 | 0.05 | 0.05 | 0.05 | 0.05 |
| | Citric acid | 0.1 | 0.1 | 0.1 | 0.1 | 0.1 | 0.1 | 0.1 | — |
| | Glycolic acid | — | — | — | — | — | — | — | 1 |

TABLE 5-1-continued

| Component | Example 2-1 | Example 2-2 | Example 2-3 | Example 2-4 | Example 2-5 | Example 2-6 | Example 2-7 | Example 2-8 |
|---|---|---|---|---|---|---|---|---|
| Salicylic acid | — | — | — | — | — | — | — | 0.5 |
| Tromethamine | — | — | — | — | — | — | — | — |
| 3-O-ethyl ascorbic acid (vitamin C derivative) | 10 | 10 | 10 | 10 | 10 | 15 | 20 | 10 |
| Niacinamide | — | — | | | | — | — | 6 |
| Caffeine | — | — | | | | — | — | 0.5 |
| Ethyl hexyl glycerin | 0.05 | 0.05 | 0.05 | 0.05 | 0.05 | 0.05 | 0.05 | 0.05 |
| 1,2-Hexanediol | 1 | 1 | 1 | 1 | 1 | 1 | 1 | 1 |

* Each number in the table above represents part by weight.

TABLE 5-2

| | Component | Comparative Example 2-1 | Comparative Example 2-2 | Comparative Example 2-3 | Comparative Example 2-4 | Comparative Example 2-5 | Comparative Example 2-6 |
|---|---|---|---|---|---|---|---|
| Silicone oil phase portion | PCA dimethicone | — | 3 | 3 | 2 | 7 | 3 |
| | Vinyl dimethicone/ Methicone silsesquioxane cross-polymer (oil-absorbing powder) | 4 | 4 | 4 | 4 | 4 | 4 |
| | Phenyl trimethicone/ caprylyl methicone (silicone oil) | 7 | 7 | 7 | 7 | 7 | 7 |
| | Pentaerythrityl tetraisostearate (ester-based oil) | — | 4 | 4 | 4 | 4 | 4 |
| Aqueous phase portion | Glycerin | 5 | 5 | 5 | 5 | 5 | 5 |
| | Butylene glycol | 5 | 5 | 5 | 5 | 5 | 5 |
| | Propanediol | 5 | 5 | 5 | 5 | 5 | 5 |
| | Water | to 100 | to 100 | to 100 | to 100 | to 100 | to 100 |
| | Disodium EDTA | 0.05 | 0.05 | 0.05 | 0.05 | 0.05 | 0.05 |
| | Citric acid | 0.1 | — | — | 0.1 | 0.1 | |
| | Glycolic acid | — | — | — | | | |
| | Salicylic acid | — | — | — | | | 0.5 |
| | Tromethamine | — | — | 0.2 | — | — | |
| | 3-O-Ethyl ascorbic acid (vitamin C derivative) | 10 | 10 | 10 | 10 | 10 | 10 |
| | Niacinamide | — | — | — | | | |
| | Caffeine | — | — | — | | | |
| | Ethyl hexyl glycerin | 0.05 | 0.05 | 0.05 | 0.05 | 0.05 | 0.05 |
| | 1,2-Hexanediol | 1 | 1 | 1 | 1 | 1 | 1 |
| | Surfactant (CETYL PEG/PPG-10/ 1DIMETHICONE, ABIL EM 90) | 3 | — | — | — | — | — |

* Each number in the table above represents part by weight.

Experimental Example 2-1: Measurement of Shape and Size of Aqueous Phase Portion in Cosmetic Composition of Water in Silicone Oil (W/S) Formulation In order to confirm the shape and size of the aqueous phase portion of the cosmetic composition of the water in silicone oil (W/S) formulation, the cosmetic compositions of the water in silicone oil (W/S) formulations of Examples 2-1 to 2-8 and Comparative Examples 2-1 to 2-6 were observed through an optical microscope.

Three of the cosmetic compositions of the water in silicone oil (W/S) formulation of Examples 2-1 to 2-8 and Comparative Examples 2-1 to 2-6 were prepared, respectively, and then the longest radius of the particles constituting the aqueous phase portions in the cosmetic compositions of the water in silicone oil (W/S) formulations of Examples 2-1 to 2-8 and Comparative Examples 2-1 to 2-6 was measured through the optical microscope, and the average number of particles having the longest radius of 5 μm or more was evaluated.

In addition, the average ratio of particles satisfying the following equation was evaluated:

$$0.8 \times (a+b) > a'+b' > 0.95 \times (a+b)$$

wherein a refers to the longest radius of one particle, b refers to the longest radius of the particle adjacent to the above particle, a' refers to the distance from the center of gravity of one particle to the outermost point on a straight line connecting the center of gravity of the above particle and the center of gravity of the adjacent particle, and b' refers to the distance from the center of gravity of the adjacent particle to the outermost point on a straight line connecting the center of gravity of the above particle and the center of gravity of the adjacent particle.

The longest radius of the particle means the longest distance among the distances from the center of gravity of the particle to the outermost point.

As a result, it was confirmed that in the cases of Examples 2-1 to 2-8, the longest radius of the particles constituting the aqueous phase portion is 2.5 μm to 10 μm, and particles having a longest radius of 5 μm or more are contained in an amount of 50% or more within a range of 0.1 mm×0.1 mm. In addition, it was confirmed that in the cases of Examples 2-1 to 2-8, particles satisfying the above formula among particles constituting the aqueous phase portion are contained in an amount of 50 or more within a range of 0.1 mm×0.1 mm. On the other hand, it was confirmed that in the case of Comparative Example 2-1 containing surfactant, the size of the particles constituting the aqueous phase portion was very small, less than 1 μm. In addition, in the cases of Comparative Examples 2-2 and 2-3, discoloration was proceeded due to oxidation of vitamin C derivatives. In the cases of Comparative Examples 2-4 and 2-5, the long-term stability of the formulation was poor. In the case of Comparative Example 2-6, Salicylic acid powder due to non-dissolution of salicylic acid was observed.

TABLE 6

| | Number of particles with a longest radius of 5 μm or more | Proportion of particles that satisfy the above equation |
|---|---|---|
| Example 2-1 | 175 | 90% |
| Example 2-2 | 220 | 80% |
| Example 2-3 | 210 | 85% |
| Example 2-4 | 225 | 75% |
| Example 2-5 | 230 | 75% |
| Example 2-6 | 220 | 80% |
| Example 2-7 | 220 | 80% |
| Example 2-8 | 210 | 80% |
| Comparative Example 2-1 | As shown in FIG. 3, the particle size is very small, 0.5 to 1 μm. In addition, general circular particles are formed, not particles satisfying the above equation. | |
| Comparative Example 2-2 | discoloration | 80% |
| Comparative Example 2-3 | discoloration | 80% |
| Comparative Example 2-4 | The long-term stability of the formulation is poor. | |
| Comparative Example 2-5 | The long-term stability of the formulation is poor. | |
| Comparative Example 2-6 | Salicylic acid powder is shown due to non-dissolution of salicylic acid. | |

Experimental Example 2-2: pH Measurement of Cosmetic Composition of Water in Silicone Oil (W/S) Formulation The pH of the aqueous phase portion of the cosmetic composition of the water in silicone oil (W/S) formulations of Examples 2-1 to 2-8 and Comparative Examples 2-1 to 2-6 and the entire cosmetic composition was measured. The pH of the entire cosmetic composition was measured after stirring the mixture at a ratio of 1:10 of cosmetic composition:distilled water at 80° C. for 10 minutes by an agitator.

As a result, it was confirmed that pH of the aqueous phase portions of the cosmetic compositions of the water in silicone oil (W/S) formulations of Examples 2-1 to 2-8 was 3.4 to 4.0, and pH of the entire cosmetic composition was 4.3 to 5.0.

The details are as shown in the table below.

TABLE 7

| | pH of aqueous phase portion | pH of entire cosmetic composition |
|---|---|---|
| Example 2-1 | 3.8 | 4.3 |
| Example 2-2 | 3.8 | 4.3 |
| Example 2-3 | 3.8 | 4.3 |
| Example 2-4 | 3.8 | 4.3 |
| Example 2-5 | 3.8 | 4.3 |
| Example 2-6 | 3.7 | 4.4 |
| Example 2-7 | 3.7 | 4.5 |
| Example 2-8 | 3.9 | 4.6 |
| Comparative Example 2-1 | 3.8 | 4.8 |
| Comparative Example 2-2 | 6.2 | 6.5 |
| Comparative Example 2-3 | 8.2 | 7.9 |
| Comparative Example 2-4 | 3.8 | 4.4 |
| Comparative Example 2-5 | 3.8 | 4.4 |
| Comparative Example 2-6 | — (Non-dissolution of salicylic acid) | — |

Experimental Examples 2-3: Evaluation of Stability Over Time and Discoloration with Time of Cosmetic Composition of Water in Silicone Oil (W/S) Formulation In order to confirm the stability over time of the cosmetic composition of the water in silicone oil (W/S) formulation, the cosmetic compositions of Examples 2-1 to 2-8 and Comparative Examples 2-1 to 2-6 were put in a 100 mL PET container and set at 45° C. in an incubator (Manufacturer: JISICO, Model name: J-100M Incubator), and stored for 8 weeks. Thereafter, the viscosity was measured for 2 minutes at a rate of 12 rpm with 64 spindles using a viscometer (Manufacturer: Brookfield, Model name: LVDV-II+P), and the presence or absence of discoloration was observed.

In addition, the cosmetic compositions of Examples 2-1 to 2-8 and Comparative Examples 2-1 to 2-6 were put in a 100 mL PET container and set at −15° C. in an incubator (Manufacturer: JISICO, Model name: J-100M Incubator), and stored for 8 weeks. Thereafter, the viscosity was measured for 2 minutes at a rate of 12 rpm with 64 spindles using a viscometer (Manufacturer: Brookfield, Model name: LVDV-II+P).

As a result, it was confirmed that the stability of the formulation was maintained, even after the cosmetic compositions of Examples 2-1 to 2-8 were stored at high and low temperatures for a long period (8 weeks). On the other hand, it was confirmed that in the cases of Comparative Examples 2-1, 2-4, and 2-5, as the aqueous phase portion was transuded from the water in silicone oil (W/S) formulation, the formulation was unstable. In addition, the cosmetic compositions of Examples 2-1 to 2-8 having a pH of 4.0 to 4.5 do not discolor even after storage for a long time, but the compositions of Comparative Examples 2-2, 2-3 and 2-5 are discolored yellow when stored for a long time at high temperature. That is, it was confirmed that in the cases of Comparative Examples 2-2, 2-3, and 2-5, the vitamin C derivative is oxidized and its activity is decreased.

The detailed results are shown in Table 8 below.

TABLE 8

| | High temperature stability (45° C., 8 weeks) | Presence or absence of discoloration(45° C., 8 weeks) | Low temperature stability (−15° C., 8 weeks) |
|---|---|---|---|
| Example 2-1 | 22500 | absence | 21900 |
| Example 2-2 | 35000 | absence | 29000 |
| Example 2-3 | 24000 | absence | 22800 |
| Example 2-4 | 24800 | absence | 21600 |
| Example 2-5 | 26000 | absence | 21500 |
| Example 2-6 | 21300 | absence | 20700 |
| Example 2-7 | 21200 | absence | 19700 |
| Example 2-8 | 22300 | absence | 20300 |
| Comparative Example 2-1 | 35000 (Water was transuded) | absence | Separation of formulation |
| Comparative Example 2-2 | 23200 | presence | 22000 |
| Comparative Example 2-3 | 23700 | presence | 22300 |
| Comparative Example 2-4 | 18700 | absence | 14000 (Water was transuded, Commencement of separation of formulation) |
| Comparative Example 2-5 | 20300 | absence | 16800 (Water was slightly transuded) |
| Comparative Example 2-6 | — | — | — |

* The unit of viscosity in the above table is cps.

As can be seen through the above Experimental Examples 2-1 to 2-4, it was confirmed that the cosmetic composition of the water in silicone oil (W/S) formulation, which contains an emollient having a pyrrolidone carboxylic acid group, an oil-absorbing powder and a silicone oil as a oil phase portion, contains water, vitamin C or vitamin C derivatives and a pH adjusting agent as an aqueous phase portion, and contains a surfactant in an amount of 0.1 wt. % or less, has excellent formulation stability, as compared to the case that does not contain emollient having a pyrrolidone carboxylic acid group (Comparative Example 2-1) and the cases that contains emollient having a pyrrolidone carboxylic acid group in an amount of less than 3 wt. % or more than 6 wt. % (Comparative Examples 2-4 and 2-5), and is excellent in stability of vitamin C derivatives because discoloration does not occur, as compared to the cases that do not contain an acidic pH adjusting agent (Comparative Examples 2-2 and 2-3).

Therefore, it was found that when the cosmetic composition of the present invention is used, even if no surfactant is used, not only the water in silicone oil (W/S) formulation can be stably formed and the stability over time of the water in silicone oil (W/S) formulation can be maintained even when stored for a long period of time at high and low temperature conditions, but also the stability of vitamin C or vitamin C derivatives contained in the aqueous phase portion is excellent.

What is claimed is:

1. A surfactant-free cosmetic composition which is a water in silicone oil (W/S) formulation comprising a silicone oil phase portion and an aqueous phase portion,
    wherein the silicone oil phase portion contains an emollient having a pyrrolidone carboxylic acid group, oil-absorbing powder, and silicone oil, and the aqueous phase portion contains water;
    wherein a content of the aqueous phase portion is 75 wt % or more and 83% or less based on a total weight of the surfactant-free cosmetic composition;
    wherein the surfactant of the surfactant-free cosmetic composition is selected from the group consisting of polyethylene glycol (PEG), lauryl polyglyceryl-3-polydimethylsiloxyethyl dimethicone, lauryl PEG-9-polydimethylsiloxyethyl dimethicone, and PEG-10 dimethicone;
    wherein the content ratio of the emollient having the pyrrolidone carboxylic acid group and the oil-absorbing powder is 1.5:1 to 1:1.5;
    wherein the weight ratio of a total amount of the emollient having the pyrrolidone carboxylic acid group plus the oil-absorbing powder to an amount of the silicone oil is 10:11 to 7:11; and
    wherein said composition is not solid at room temperature.

2. The surfactant-free cosmetic composition according to claim 1, wherein the emollient having the pyrrolidone carboxylic acid group is pyrrolidone carboxylic acid (PCA) dimethicone.

3. The surfactant-free cosmetic composition according to claim 1, wherein the oil-absorbing powder is one or more selected from the group consisting of vinyl dimethicone/methicone silsesquioxane cross-polymer, POLYSILICONE-11, POLYSILICONE-13, diphenyl dimethicone/vinyl diphenyl dimethicone/silsesquioxane cross-polymer, dimethicone/vinyl dimethicone cross-polymer, dimethicone/phenylvinyl dimethicone cross-polymer, and polymethyl silsesquioxane.

4. The surfactant-free cosmetic composition according to claim 1, wherein the silicone oil is one or more selected from the group consisting of methicone-based silicone oil, dimethicone-based silicone oil, cyclomethicone-based silicone oil, and phenyl trimethicone-based silicone oil.

5. The surfactant-free cosmetic composition according to claim 1, wherein the aqueous phase portion contains 79 wt. % or more and 82 wt. % or less of water, based on the total weight of the surfactant-free cosmetic composition.

6. The surfactant-free cosmetic composition according to claim 1, wherein each of the emollient having the pyrrolidone carboxylic acid group and the oil-absorbing powder is 2 wt. % or more and 6 wt. % or less based on the total weight of the surfactant-free cosmetic composition.

7. The surfactant-free cosmetic composition according to claim 1, wherein the aqueous phase portion further comprises vitamin C or a vitamin C derivative and a pH adjusting agent, the aqueous phase portion is composed of a plurality of particles, and the particles comprise particles having a longest radius of 2.5 to 10 μm.

8. The surfactant-free cosmetic composition according to claim 1, wherein the silicone oil phase portion further comprises an ester-based oil.

9. The surfactant-free cosmetic composition according to claim 8, wherein the ester-based oil is one or more selected from the group consisting of ethylhexyl isononanoate, myristyl lactate, cetyl octanoate, ethylhexyl isopalmitate, ethylhexyl isostearate, ethylhexyl myristate, isopropyl myristate, isopropyl palmitate, isocetylethyl hexanoate, octyldodecyl myristate, octyldodecyl stearoyl stearate, ethyl hexyl neopentanoate, ethyl hexyl oleate, ethyl hexyl palmitate, ethyl hexyl stearate, isononyl isononanoate, polyglyceryl-2 triisostearate, pentaerythrityl tetraisostearate, pentaerythrityl tetraethyl hexanoate, cetylethyl hexanoate, diisostearyl malate, caprylic/capric triglyceride, dicaprylyl carbonate, neopentyl glycol dicaprate, butylene glycol dicaprylate/caprate, hexyl laurate, glyceryl triethyl hexanoate, and diglyceryl triisostearate.

10. The surfactant-free cosmetic composition according to claim 7, wherein the vitamin C derivative is one or more selected from the group consisting of sodium ascorbyl phosphate (SAP), magnesium ascorbyl phosphate (MAP), calcium ascorbyl phosphate, ascorbic acid polypeptide, 3-O-ethyl ascorbic acid, ascorbyl dipalmitate, ascorbyl palmitate, ascorbyl stearate, ascorbyl glucoside, and ascorbyl ethyl silanol pectinate.

11. The surfactant-free cosmetic composition according to claim 7, wherein the pH adjusting agent is one or more selected from the group consisting of malic acid, citric acid, acetic acid, propionic acid, oxalic acid, glycolic acid, malonic acid, lactic acid, succinic acid, tartaric acid, aspartic acid, maleic acid, glutaric acid, glutamic acid, gluconic acid, sorbic acid, benzoic acid, ascorbic acid and salicylic acid.

12. The surfactant-free cosmetic composition according to claim 7, wherein the aqueous phase portion further comprises niacinamide and caffeine.

13. The surfactant-free cosmetic composition according to claim 7, wherein the aqueous phase portion has a pH of 3.0 to 4.0.

14. The surfactant-free cosmetic composition according to claim 7, wherein the aqueous phase portion contains 50% or more of particles having a shape satisfying the following equation within an area of 0.1 mm×0.1 mm:

$$0.8 \times (a+b) > a' + b' > 0.95 \times (a+b)$$

wherein a refers to the longest radius of one particle,
b refers to the longest radius of the particle adjacent to the above particle,
a' refers to the distance from the center of gravity of one particle to the outermost point on a straight line connecting the center of gravity of the above particle and the center of gravity of the adjacent particle, and
b' refers to the distance from the center of gravity of the adjacent particle to the outermost point on a straight line connecting the center of gravity of the above particle and the center of gravity of the adjacent particle.

15. The surfactant-free cosmetic composition according to claim 7, wherein the aqueous phase portion contains 100 or more particles having a size of 5 μm or more in the longest radius within an area of 0.1 mm×0.1 mm.

16. The surfactant-free cosmetic composition according to claim 7, wherein the entire cosmetic composition of the silicone water-in-oil (W/S) formulation has a pH of 4.3 to 5.0.

17. The surfactant-free cosmetic composition according to claim 7, wherein the content of the vitamin C or vitamin C derivative is 10 wt. % or more based on the total weight of the cosmetic composition.

* * * * *